(12) United States Patent
Petter et al.

(10) Patent No.: US 12,402,582 B2
(45) Date of Patent: *Sep. 2, 2025

(54) SHALLOT PLANT NAMED 'INNOVATOR'

(71) Applicants: Bejo Zaden B.V., Warmenhuizen (NL); De Groot en Slot B.V., Broek op Langedijk (NL)

(72) Inventors: Timo Christiaan Petter, Warmenhuizen (NL); Lennaert Crispijn Aardse, Broek op Langedijk (NL)

(73) Assignees: Bejo Zaden B.V., Warmenhuizen (NL); De Groot en Slot B.V., Broek op Langedijk (NL)

( * ) Notice: Subject to any disclaimer, the term of this patent is extended or adjusted under 35 U.S.C. 154(b) by 401 days.

This patent is subject to a terminal disclaimer.

(21) Appl. No.: 17/991,915

(22) Filed: Nov. 22, 2022

(65) Prior Publication Data

US 2023/0180692 A1   Jun. 15, 2023

Related U.S. Application Data

(60) Provisional application No. 63/287,762, filed on Dec. 9, 2021.

(51) Int. Cl.
*A01H 5/04* (2018.01)
*A01H 6/04* (2018.01)

(52) U.S. Cl.
CPC ............... *A01H 6/045* (2018.05); *A01H 5/04* (2013.01)

(58) Field of Classification Search
None
See application file for complete search history.

(56) References Cited

U.S. PATENT DOCUMENTS

| 8,119,856 B2 * | 2/2012 | Harrewijn | A01H 6/045 800/278 |
| 8,697,359 B1 | 4/2014 | Zhang | |
| PP35,020 P2 * | 3/2023 | Petter | A01H 6/045 Plt./263.1 |

FOREIGN PATENT DOCUMENTS

WO   2014/076249 A1   5/2014

OTHER PUBLICATIONS

Reflinur et al., "Phenotypic Evaluation and Genetic Profiling of Shallot Genotypes Adapted to Peatland of South Kalimantan Using Simple Sequence Repeat (SSR) Markers," Agrivita, Journal of Agricultural Science 2019, 41(1), 74-87.

Wijinker et al. "Hybrid recreation by reverse breeding in *Arabidopsis thaliana*," Nature Protocols 2014, 9: 761-772.

* cited by examiner

*Primary Examiner* — Russell Kallis
(74) *Attorney, Agent, or Firm* — The Webb Law Firm

(57) ABSTRACT

Provided herein is shallot variety 'Innovator,' including seeds thereof and methods of using the variety to generate additional shallot varieties. The variety is characterized by its color, size, shape, and resistance to *P. destructor*.

12 Claims, 7 Drawing Sheets
(4 of 7 Drawing Sheet(s) Filed in Color)

| female ♀ | | |
|---|---|---|
| | | |
| | | |
| | | |
| | | |
| | | |
| | | |
| | | |
| | | |
| | | Local French ♂ maintainer inbred line nr 2 |
| Local French elite ♀ line (BC 0) | X | Local French ♂ maintainer inbred line nr 2 |
| | ↓ | |
| Local French elite ♀ line (BC 1) | X | Local French ♂ maintainer inbred line nr 2 |
| | ↓ | |
| Local French elite ♀ line (BC 2) | X | Local French ♂ maintainer inbred line nr 2 |
| | ↓ | |
| Local French elite ♀ line (BC 3) | X | Local French ♂ maintainer inbred line nr 2 |
| | ↓ | |
| Increasing elite ♀ line nr 2 | X | Increasing elite ♂ maintainer line nr 2 |
| ↓ | | |
| Making cross elite ♀ line nr 2 | | |

*FIG. 5*

| male ♂ | |
|---|---|
| | introgression of Pd-R from *A.roylei* into French shallot elite breeding line by emasculation of *A. roylei* |
| | Creating F2 from heterozygous Pd-R F1 of *A.roylei* x French Shallot elite breeding line |
| | Selfing of Pd-R F2 of *A.roylei* x French Shallot elite breeding line (F2S1) |
| | ↓ |
| French shallot elite ♂ breeding line with N_msms    X | homozygous Pd-R inbred line of *A.roylei* x French Shallot elite breeding line |
| ↓ | |
| Creating F2 from heterozygous Pd-R F1 | |
| ↓ | |
| Selfing of homozygous Pd-R and N_msms French shallot elite ♂ breeding line (F2S1) | |
| ↓ | |
| homozygous Pd-R and N_msms French shallot ♂ inbred line nr 3 | |
| ↓ | |
| Maintaining homozygous Pd-R and N_msms French shallot ♂ inbred line nr 3 | |
| ↓ | |
| Maintaining homozygous Pd-R and N_msms French shallot ♂ inbred line nr 3 | |
| ↓ | |
| Increasing homozygous Pd-R and N_msms French shallot ♂ inbred line nr 3 | |
| | |
| homozygous Pd-R ♂ inbred line nr 3 | |

*FIG. 6*

| Making cross elite ♀ line nr 2 | | X | homozygous Pd-R ♂ inbred line nr 3 |
|---|---|---|---|
| | Testing cross | ↓ | |
| | Testing cross | ↓ | |
| | Testing cross | ↓ | |
| Decision making Innovator F1 | | | |

*FIG. 7*

SHALLOT PLANT NAMED 'INNOVATOR'

CROSS-REFERENCE TO RELATED APPLICATIONS

The present application claims the benefit of U.S. Provisional Patent Application No. 63/287,762, filed Dec. 9, 2021, the disclosure of which is incorporated herein by reference in its entirety. The present application is related to U.S. patent application Ser. No. 17/300,896, the disclosure of which is incorporated herein by reference in its entirety.

FIELD OF THE INVENTION

Disclosed herein is a new variety of shallot.

BACKGROUND OF THE INVENTION

Shallots are an important cultivated crop. Cultivars of the onion (*Allium cepa*), shallots, classified in *A. cepa* var. *aggregatum*, possess a milder flavor and are used in a number of cuisines in Europe and Asia. Shallots, and other *Allium*, are typically susceptible to pathogens, including *Peronospora destructor*, which can cause downy mildew on the leaves of *Allium*. Downy mildew can affect both the outward appearance of shallots, as well as production of useful bulbs. Therefore, it is desirable to develop new varieties of shallot having exceptional traits, including resistance to pathogens, such as *P. destructor*.

SUMMARY OF THE INVENTION

Provided herein is shallot variety 'Innovator', characterized by its color, size, and resistance to *P. destructor*. In one aspect, seed of shallot variety 'Innovator' is provided. Seed of variety 'Innovator' has been deposited with NCIMB under Accession No. 43895.

Also provided herein are plants grown from seed of variety 'Innovator', and plant parts and seeds produced by plants so grown.

Also provided herein are methods of generating offspring of variety 'Innovator', including the steps of crossing a plant of variety 'Innovator' with a second variety of shallot plant. In some aspects, both plants are variety 'Innovator'. In other aspects, the second variety is selected for a desired trait which can be introduced into offspring, such that said offspring include physiological/morphological traits of variety 'Innovator' and the desired trait(s) of the second variety.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5 shows breeding history of a parental line of variety 'Innovator';
FIG. 6 shows breeding history of a parental line of variety 'Innovator';
and
FIG. 7 shows breeding history of variety 'Innovator'.

DESCRIPTION OF THE INVENTION

Figure 1:
FIG. 1 shows variety 'Innovator'.

In the description and table which follow, a number of terms are used. To provide a clear and consistent understanding of the specification and claims, including the scope to be given such terms, the following definitions are provided:

Amplified Fragment Length Polymorphism (AFLP®): A PCR-based method of identifying polymorphisms through digestion with known restriction enzymes followed by visualization through use of radiography or fluorescence.

Allele: The allele is any of one or more alternative forms of a gene, all of which relate to one trait or characteristic. In a diploid cell or organism, the two alleles of a given gene occupy corresponding loci on a pair of homologous chromosomes.

Backcrossing: Backcrossing is a process in which a breeder repeatedly crosses hybrid progeny back to one of the parents, for example, a first generation hybrid F1 with one of the parental genotype of the F1 hybrid.

BC1: First backcross generation.

Cleaved Amplified Polymorphic Sequence (CAPS): A method of identifying genetic markers based on the length of restriction fragment lengths. Restriction fragments analyzed using CAPS are typically generated using a Restriction Fragment Length Polymorphism assay.

Cotyledon: One of the first leaves of the embryo of a seed plant, typically one or more in monocotyledons, two in dicotyledons, and two or more in gymnosperms.

Clustered Regularly Interspaced Short Palindromic Repeats (CRISPR): Refers to DNA sequences found in bacteria that include portions of DNA introduced to the bacteria by a given virus. The concept is the basis of the CRISPR system of editing an organism's genome (see, e.g., U.S. Pat. No. 8,697,359, incorporated herein by reference in its entirety).

CRISPR-Associated System (CAS): A set of homologous genes, encoding enzymes, that reside in the genome near the site of CRISPR sequences. These enzymes target DNA sequences based on similarity to the viral sequences included in the CRISPR regions.

Embryo: A plant embryo is a portion of the seed including precursors of the leaves, stem, and root, and one or more cotyledons.

F1, F2, F3 etc.: First, second, third, etc. filial generation of offspring of distinctly different parental types.

First water date: The date the seed first receives adequate moisture to germinate. This can and often does equal the planting date.

Gene: As used herein, "gene" refers to a segment of nucleic acid. A gene can be introduced into a genome of a species, whether from a different species or from the same species, using transformation or various breeding methods.

Genetically-Modified Organism (GMO): An organism whose genome has been altered using some form of genetic engineering.

Hypocotyl: The portion of the stem of an embryo plant beneath the cotyledons, but above the root.

Marker-assisted recurrent backcrossing (MARB): A method of introducing a single locus of interest. The MARB method allows for maintenance of essential characteristics of the recurrent parent's genome. MARB is particularly effective for Quantitative Trait Loci (QTLs) that are highly variable.

Marker-assisted selection (MAS): A method of selecting a trait of interest based not on the trait, but on a marker associated with that trait.

Maturity date: Maturity refers to the stage when the plants are of full size or optimum weight, in marketable form or shape to be of commercial or economic value.

Meristematic cell: Cells of the meristem, which is a collection of undifferentiated cells in the plant. Meristematic cells include apical meristematic cells and lateral meristematic cells.

*Peronospora destructor*: A plant pathogen that causes downy mildew on leaves of cultivated and wild *Allium*.

Pest: A bacterium, fungus, virus, insect, or animal that attacks or negatively affects a plant.

Plant: "Plant" includes plant cells, plant protoplasts, plant cells of tissue culture from which shallot plants can be regenerated, plant calli, plant clumps, and plant cells that are intact in plants, or parts of plants such as pollen, flowers, seeds, leaves, stems and the like.

Promoter: A region of DNA upstream from the start of transcription and involved in recognition and binding of RNA polymerase and other proteins to initiate transcription. A "plant promoter" is a promoter capable of initiating transcription in plant cells.

Protoplast: A plant cell that has had its cell wall at least partially removed.

Quantitative Trait Loci (QTL): Refers to genetic loci that control, to some degree, numerically representable traits that are usually continuously distributed.

Random Amplified Microsatellite Polymorphism (RAMP): A PCR-based method of identifying polymorphisms through use of simple sequence repeat markers and random amplified DNA polymorphism markers. RAMP is particularly useful for assessing genetic relationships in plant species.

Random Amplified DNA Polymorphism: A PCR-based method of amplifying random sections of DNA.

Ratio of head height/diameter: Head height divided by the head diameter is an indication of the head shape with <1 is flattened, 1=round, and >1 is pointed.

Recurrent Parent: The backcross parent, and member of an identifiable lineage or line that is improved by addition of a trait not found in that line.

Regeneration: Regeneration refers to the development of a plant from tissue culture.

Resistance: The character of a plant to restrict or even inhibit the development of a pest or pathogen in or on the plant and also the restriction of damage these organisms may cause in comparison to a susceptible variety and under comparable circumstances.

Restriction Fragment Length Polymorphism (RFLP): A marker in homologous DNA detectable based on fragments of different, specific lengths generated by known restriction enzymes.

Root tip: The terminal portion of the root of a plant.

Royal Horticultural Society of England (RHS): An organization that publishes an official botanical color chart quantitatively identifying colors according to a defined numbering system. The chart may be purchased from Royal Horticulture Society Enterprise Ltd., RHS Garden; Wisley, Woking; Surrey GU236QB, UK. As used herein, references to RHS color refer to those in the Sixth Edition (2019) of the chart.

Simple sequence repeats (SSR): A DNA sequence having a number of motifs that are repeated.

Single nucleotide polymorphism (SNP): A common nucleotide variation at a given locus among a given population.

Transgenic: An organism that contains genetic material from an unrelated organism that has been artificially introduced.

Shallot Variety 'Innovator'

Provided herein is shallot variety 'Innovator'. Shallot variety 'Innovator' is the result of a cross between two parent lines. The breeding histories for these lines is shown in FIGS. 5 and 6. The variety 'Innovator' was selected following breeding as shown in FIG. 7. These plants were chosen for resistance to *P. destructor*, excellent storability of the bulb, uniformity in crop growth, and marketable produce. Variety 'Innovator' exhibits bulbs in the form of a number of bulblets, and the tendency to split into bulblets is weak. Variety 'Innovator' exhibits similar internal color and time to harvest maturity as its parental lines, while differing in shape and color of dry skin. With regard to other varieties, 'Innovator' exhibits differences in bulblet size, shape, hue of color of dry skin, and the noted resistance to *P. destructor*.

Shallot variety 'Innovator' has shown uniformity and stability for these traits with limited environmental influence on the traits. It has been self-pollinated through a sufficient number of generations with careful attention to uniformity of plant type. The variety has been propagated with continuous attention for uniformity.

Breeding History

Crosses, for example as shown in FIG. 7, were made by spraying or misting water over the flowers, thereby inactivating pollen present on these flowers. This treatment enables the cross pollination of *Allium* plants.

F1 plants can be self-pollinated to produce the F2 generation, etc.

As noted above, parental lines, produced as shown in FIGS. 5 and 6, were used, and variety 'Innovator' was produced as shown in FIG. 7. Briefly, an interspecific cross was made by emasculation between the *P. destructor* resistant (Pd-R) species *A. roylei* and a Pd susceptible generative male fertile shallot breeding line. F2S1 individuals were derived from this cross and screened and selected for homozygosity on the Pd-R trait, phenotypic uniformity, plant vigor and seed producibility. A cross was then made between a male fertile shallot maintainer line and one of the F2S1 Pd-R individuals selected. F2S1 individuals were derived again and Pd-R inbred line no. 3 was selected. Pd-R inbred line 3 was screened and selected on homozygosity on the Pd-R trait, important agronomic traits, bulb storability, and flowering behavior. A hybrid cross was then made between CMS shallot elite line no. 2 and Pd-R line 3. This hybrid cross was extensively tested at trial fields over Northern Europe and the United States, and the cross was named Innovator F1 and selected for commercialization.

Seeds of all plants from this best-performing line were collectively harvested and designated variety 'Innovator'. A deposit of seeds of 'Innovator' as disclosed above and recited in the appended claims has been made with the National Collections of Industrial, Food and Marine Bacteria (NCIMB), Ferguson Building, Craibstone Estate, Bucksburn, Aberdeen AB21 9YA, United Kingdom. The date of the deposit was Nov. 24, 2021. All restrictions will be irrevocably removed upon granting of a patent, and the deposit is intended to meet all of the requirements of 37 C.F.R. § 1.801-1.809. The NCIMB Accession Number is 43895. The deposit will be maintained in the depository for a period of thirty years, or five years after the last request, or for the enforceable life of the patent, whichever is longer, and will be replaced as necessary during that period.

Variety Description

Shallot variety 'Innovator' is a seed-propagated shallot which is a single-cross hybrid. Variety 'Innovator' is resistant to at least *P. destructor*. Shallot variety 'Innovator' is similar to the variety 'Conservor', in that both are seed-propagated hybrids and exhibit suitability for storage. As used herein, "similarity" is defined as the number of distinguishing characteristics that are the same between the two plants that are compared when grown under the same environmental conditions. Characteristics are considered "the same" when the value for a numeric characteristic is evaluated at significance levels of 1%, 5% or 10% significance level, or when a non-numeric characteristic is identical, if the plants are grown under the same conditions. With regard to this comparison, variety 'Innovator', exhibits a larger bulblet size (at 8 months) than 'Conserver' and exhibits a more elongated bulblet shape (at 8 months) than 'Conserver'. 'Innovator' also exhibits a different dry skin color than 'Conserver' (RHS 176C for 'Innovator' and RHS 177C for 'Conserver'). Variety 'Innovator' exhibits strong resistance to *P. destructor*, while 'Conserver' does not. Moreover, the bulblet weight and scales (thickness and amount) of 'Innovator' are distinguishable from 'Conserver', and the root system of 'Innovator' is more vigorous than that of 'Conserver'. Variety 'Innovator' can be asexually reproduced by splitting and replanting bulblets in soil, and can also be sexually reproduced.

Characteristics of variety 'Innovator' in concordance with the applicable UPOV Questionnaire (Guidelines for the Conduct of Tests for Distinctness, Uniformity and Stability, TG/46/7 (Geneva 2009)), are provided below:

Bulb shape in longitudinal section: Elliptic.
Height from soil line to top of bulb: Approximately 6-7 cm.
Leaf length: Approximately 40-60 cm.
Sheath height from soil line to base of lowest succulent leaf: Approximately 7-8 cm (before maturity yellowing begins).
Hardiness: Bulb can be very firm up to 5 months after harvest.
Rooting: Vigorous.
Disease resistance: Highly resistant to *Peronospora destructor*.
Tendency to bolt trials: Not suitable for Autumn sowing and Spring sown bolting tendency is very low—an approximate bolting time is not able to be provided.
Foliage:
    Attitude: Semi-erect.
    Waxiness: Thin and matte waxy layer present, having a color blend of RHS 189A and 189B.
    Cracking: None observed to date.
    Pseudostem length: 9 cm.
    Leaves:
    Number: Approximately 6-10 leaves per plant.
    Attachment and arrangement: Arranged on the disc-like pseudo stem in concentric circles.
    Length: Approximately 40-60 cm.
    Width: Approximately 1-2 cm.
    Aspect: Upright.
    Shape: Narrow.
    Apex: Pointed.
    Venation: Longitudinal, parallel veins present.
    Margin: Entire.
    Fragrance: Delicate, aromatic, and much sweeter than onion leaves.
    Texture: Smooth (both surfaces).
    Color: RHS 143A (both surfaces).

Bulbs:
    Height: Tall to very tall, approximately 6-7 cm.
    Width: Approximately 3-5 cm at widest point (the middle), with a neck of average size.
    Shape: Elliptic in longitudinal section, with a strongly tapered root end.
    Weight: Approximately 70 grams.
    Coloration of epidermis of fleshy scales: RHS 70B (immediately after harvest).
    Dried skin color (3 months after harvest): RHS 176C.
    Adherence of skin after harvest: Strong.
    Thickness of dried skin: Average.
    Flesh color: RHS 196D in the center, transitioning to RHS 70B toward the scales.
    Taste: Delicate and sweet with a hint of sharpness.
    Smell: Delicate, aromatic, and much sweeter than onions.
    Eating quality: Good and mild.
    Keeping quality: Suitable for long term storage.
    Bulblets: Observed with weak tendency.
Flowers:
    Inflorescence:
    Type: Umbel.
    Lastingness: 10 days.
    Size: 8.1 cm in depth and 8.1 cm in diameter.
    Fragrance: Faint and sweet.
    Number of flowers per inflorescence: Approximately 600.
    Bud:
    Length: 4 mm.
    Width: 3 mm.
    Shape: Ovate, triangular in cross section.
    Color: RHS 155C, with RHS 143B main veins of immature tepals.
    Form: Single.
    Length: 1 cm.
    Width: 1 cm.
    Tepals:
    Number: 6 per flower.
    Shape:
        Upper tepals: Oblong and slightly concave.
        Lower tepals: Ovate and slightly concave.
    Length:
        Upper tepals: Average of 5.5 mm.
        Lower tepals: Average of 4.0 mm.
    Width:
        Upper tepals: Average of 2.0 mm.
        Lower tepals: Average of 1.5 mm.
    Apex:
        Upper tepals: Abruptly acute.
        Lower tepals: Acute.
    Base: Broadly cuneate.
    Margin: Entire.
    Texture: Smooth and glabrous (both surfaces).
    Color:
        Fully opened, upper side: Upper and lower tepals are RHS N155A.
        Fully opened, under side: Upper tepals are RHS NN155D and lower tepals are RHS 155C.
    Stem (Peduncle):
    Number per plant: 1.
    Shape: Elliptic.
    Length: Average of 131.3 cm.
    Diameter: Average of 2.1 cm at widest, flattened point and average of 1.7 cm at narrowest, flattened point.
    Surface: Smooth, glabrous, and covered with a very thin waxy layer.

Color: RHS NN137B.
Pedicel:
  Shape: Circular.
  Length: Average of 3.2 cm.
  Width: Average of 1 mm.
  Surface: Smooth, glabrous, moderately glossy.
  Color: RHS 138A and fading to RHS 144B towards the base.
Reproductive Organs (100% Male Sterility):
  Gynoecium:
  Pistils:
    Number: Average of 1 per flower.
    Length: Average of 3.5 mm.
  Stigma:
    Width: Average of 0.2 mm.
    Color: RHS NN155D.
  Styles:
    Length: Average of 3 mm.
    Color: RHS NN155D.
  Ovary:
    Diameter: 3 mm.
    Color: RHS 157D, with RHS 143B veins.
  Androecium:
  Stamens:
    Number: Average of 6 per flower.
    Length: Average of 6 mm.
  Anthers:
    Length: Average of 1 mm.
    Color: RHS N148D.
  Pollen:
    Color: RHS 161D.
    Amount: Low.
  Filaments:
    Length: Average of 5 mm.
    Color: RHS NN155C.
Fruit/seeds: None observed to date.

Characteristics of variety 'Innovator' in concordance with the applicable UPOV Questionnaire (Guidelines for the Conduct of Tests for Distinctness, Uniformity and Stability, TG/46/7 (Geneva 2009)) as compared to the 'Conserver' variety, are provided below in Table 1.

TABLE 1

| Characteristic | 'Innovator' | 'Conserver' |
|---|---|---|
| 1. Bulblet: color | Greyed-Orange Group 176-C Greyish Reddish Orange | Greyed-Orange Group 177-C Greyish Reddish Orange |
| 2. Bulblet: Size (8 months) | Larger Diameter - 3-5 cm Width - 3-5 cm Weight - 70 g | Smaller |
| 3. Bulblet: Shape (8 months) | Elliptic, More Elongated | Less Elongated |
| 4. Bulblet: Height (from soil line to top of bulblet) | 6-7 cm | 6-7 cm |
| 5. Bulblet: Firmness after harvest | At least 5 months | At least 5 months |
| 6. Resistance to *P. destructor* | Yes, Strong | No |
| 7. Blooming time/lifecycle | Seed or bulblet to bulb - first year Bulb to flower - second year | Seed or bulblet to bulb - first year Bulb to flower - second year |
| 8. Leaf: Length | 40-60 cm | 40-60 cm |
| 9. Leaf: Number | 6-10 | 6-10 |
| 10. Leaf: Width | 1-2 cm | 1-2 cm |
| 11. Leaf: Aspect | Upright | Upright |
| 12. Leaf: Shape | Narrow | Narrow |
| 13. Leaf: Apex | Pointed | Pointed |
| 14. Leaf: Venation | Longitudinal parallel vein | Longitudinal parallel vein |
| 15. Leaf: Margin | Entire | Entire |
| 16. Leaf: Fragrance | Delicate and aromatically perfumed, sweeter than onion | Delicate and aromatically perfumed, sweeter than onion |
| 17. Leaf: Attachment | Arranged on disc-like pseudostem in concentric circles | Arranged on disc-like pseudostem in concentric circles |
| 18. Leaf: Characteristics/Texture | Smooth upper and lower surface | Smooth upper and lower surface |
| 19. Leaf: Color | Upper Surface - Green Group 143-A (Strong Yellowish Green) Lower Surface - Green Group 143-A (Strong Yellowish Green) | Upper Surface - Green Group 143-A (Strong Yellowish Green) Lower Surface - Green Group 143-A (Strong Yellowish Green) |
| 20. Scape: Color | Light Greyish Green | Light Greyish Green |
| 21. Sheath: Column length (height from soil line to base of lowest succulent leaf) | 7-8 cm (before maturity yellowing begins) | 7-8 cm (before maturity yellowing begins) |
| 22. Taste | Delicate, sweet flavor with a hint of sharpness | Delicate, sweet flavor with a hint of sharpness |
| 23. Scent | Delicate and aromatically perfumed, sweeter than onion | Delicate and aromatically perfumed, sweeter than onion |

TABLE 1-continued

| Characteristic | 'Innovator' | 'Conservor' |
| --- | --- | --- |
| 24. Eating Quality | Rich in fiber, low in calories and fat. | Rich in fiber, low in calories and fat. |
| 25. Keeping Quality | Suitable for long-term storage | Suitable for long-term storage |

Figure 2:
FIG. 2 shows variety 'Innovator'.
Figure 3:
FIG. 3 shows variety 'Innovator'.
Figure 4:
FIG. 4 shows variety 'Innovator'.

FIGS. 1-4 show images of variety 'Innovator' taken at eight months (bulblet), three months after planting (plant), and seven months after bulb planting (flower). Measurements for 'Innovator' were obtained in The Netherlands, under natural light (field observations) or LED light in an indoor research facility (post-harvest material observations). Growth conditions for 'Innovator' were maritime climatic conditions in a long-day region with more than 15 hours of daylight during the longest day. Variety 'Innovator' grows well in drained soil with a pH of about 5-7. Drilling or planting of bulblets can occur as early as the beginning of March, with harvest of bulblets at the end of August for Northern European conditions. Development of first leaves following planting/drilling is approximately 2-3 weeks.

As is typical of the species, 'Innovator' initiates bulbing when both temperature and a minimum number of daylight hours reach certain levels. When shallots are first planted, they initially develop their vegetative growth (root, pseudostem and leaf) with no sign of bulb formation until the proper day length for that specific cultivar triggers the signal to the plant to stop producing above ground vegetative growth and start forming a bulb. Shallot is thus sensitive to the period of daylight it receives, and for most cultivars it is only when a specific photo period is reached, that a bulb starts to form. Long day shallot cultivars require a minimum of 15 hours daylight for bulb formation.

With regard to the descriptors identified above in Table 1, plant variety descriptors for onion described in the "Guidelines for the Conduct of Tests for Distinctness, Uniformity and Stability, TG/46/7 (Geneva 2009), as published by UPOV (International Union for the Protection of New Varieties of Plants, available on the world wide web at upov.int) and which can be downloaded at upov.int under edocs/tgdocs/en/tg046.pdf (incorporated by reference in its entirety), were used as appropriate.

Further Embodiments

In general, breeding goals associated with development of any plant, including shallots, are: weight, size, leaf color, shape, texture, flavor, earliness, shelf life, resistances against pests and physical disorders, and hybrid production.

Breeding can be accelerated by application of several techniques, including tissue culture for enabling wide crosses and protoplast fusions. Further, significant progress has been made, as for many other vegetable crops, by applying molecular markers. Developing these markers has led to the development of increasingly detailed genetic maps.

These maps contain data from several sources and multiple populations and comprise Quantitative Trait Loci (QTLs), and markers linked to monogenic traits. These markers can be, e.g., RFLP, AFLP, CAPS, RAMP, SSR, microsatellites, and/or SNP markers, which all are well known for persons skilled in the art. Application of these techniques also enables MAS/MARB.

As noted above, one breeding goal in *A. cepa* is resistance to pests. As with many crops, shallots can be plagued with several physiological problems, like nutrient deficiencies, but also by pests (nematodes, insects, mammals, bacteria, fungi, and/or viruses) and disease caused thereby. Specific examples include bacterial diseases caused by *P. destructor*.

As noted above, knowledge of *A. cepa* genetics has allowed for extensive mapping of the genome, including 50 genes related to resistance to seven major diseases. Modern molecular techniques also make it possible to stack genes, including genes for *P. destructor* resistance.

It is feasible to introduce traits by cis-genes from *A. cepa*, or transgenes from any source, encoding novel forms of disease resistance, herbicide resistance, and resistance to pests by, among other techniques, siRNA (host induced gene silencing) as well as other methods which are common to the person skilled in the art.

These methods include, for example and without limitation, electroporation, *Agrobacterium*-mediated transformation, particle gun transformation, polyethylene glycol (PEG)-mediated protoplast transformation, and silicon whiskers transformation. Further, novel molecular techniques such as CRISPR/CAS9 can be applied for genome editing purposes. These techniques are known to those having ordinary skill in the art.

Introducing resistance to a pest or disease, either by conventional breeding or applying techniques as described above, provides an alternative to application of chemical protectants, which is expensive and also may have a negative impact on the environment, on growers, and others who work with the crop.

Further Embodiments—Genetic Engineering

With the advent of molecular biological techniques that have allowed the isolation and characterization of genes that encode specific protein products, such as those described above and incorporated by reference, scientists in the field of plant biology have a strong interest in engineering the genome of plants to contain and express foreign genes, or additional, or modified versions of native, or endogenous, genes (driven by different promoters) in order to alter the traits of a plant in a specific manner. Any DNA sequences, whether from a different species (i.e. transgenes) or from the same species (i.e. cis-genes), which are introduced into the genome using transformation or various breeding methods, are herein collectively referred to as "transgenes." Over the last fifteen to twenty years, several methods for producing transgenic plants have been developed, and the present invention, in particular embodiments, also relates to transformed versions of the aforementioned varieties. Suitable genetic engineering techniques for transforming, or introducing, traits into the shallot varieties disclosed herein include, for example and without limitation, microinjection, biolistics, electroporation, chemical poration, and transformation using vectors.

Accordingly, provided herein are methods of transforming a plant or plant part of the shallot varieties disclosed herein, or offspring thereof, by any transformation method known to those of skill in the art. A particularly common example of plant transformation involves the construction of an expression vector that will function in plant cells. Such a vector comprises DNA comprising a gene under control of, or operatively linked to, a regulatory element (for example, a promoter). The expression vector may contain one or more operably linked gene/regulatory element combinations. The vector(s) may be in the form of a plasmid, and can be used alone or in combination with other plasmids, to provide transformed plants using transformation methods known to those of skill in the art, to incorporate transgenes into the genetic material of the shallot plant(s).

The shallot variety disclosed herein and offspring thereof can be genetically engineered to express various phenotypes of agronomic interest. Examples hereof are genes that confer resistance to pests and/or herbicides, that confer or contribute to a value-added trait, and that control male sterility. Methods for transforming plants or introducing desired traits are similarly disclosed in International Patent Application Publication No. WO 2014/076249 and Wijnker et al. "Hybrid recreation by reverse breeding in *Arabidopsis thaliana*," Nature Protocols 2014, 9: 761-772, which are incorporated herein by reference in their entirety.

Further Embodiments—Additional Breeding Methods

Also provided herein are methods for producing a shallot plant by crossing a first parent shallot plant with a second parent shallot plant wherein the first or second parent shallot plant is a shallot variety disclosed herein. Plant breeding techniques, including crossing, thus crossing the shallot varieties disclosed herein with another plant (including the varieties disclosed herein), or with another variety (related or unrelated to the varieties disclosed herein) are well within the skill of the ordinary artisan. Thus, any such methods, i.a., selfing, backcrosses, hybrid production, crosses to populations, and the like, using the shallot varieties disclosed herein should be considered part of this invention. All plants produced using one or more of the shallot varieties disclosed herein as are within the scope of the disclosure, including those developed from varieties derived from the shallot varieties disclosed herein.

In aspects of a breeding method described herein, both first and second parent shallot plants are one or more of the shallot varieties disclosed herein.

In other aspects, the shallot varieties disclosed herein can be used in crosses with other, different, shallot plants to produce the first generation (F1) shallot hybrid seeds and plants with superior characteristics. The shallot varieties disclosed herein can also be used for transformation where exogenous genes are introduced and expressed. Genetic variants created either through traditional breeding methods using the shallot varieties disclosed herein or through transformation of the shallot varieties disclosed herein by any of a number of protocols known to those of skill in the art are intended to be within the scope of the present invention.

In one aspect, the method includes the steps of: obtaining the shallot plant, or a part thereof, of one or more of the shallot varieties disclosed herein, utilizing said plant or plant part as a source of breeding material, and selecting a progeny plant with molecular markers in common with one or more of the shallot varieties disclosed herein and/or with morphological and/or physiological characteristics selected from the characteristics of the shallot varieties disclosed herein listed in Table 1. Breeding steps that may be used include pedigree breeding, backcrossing, mutation breeding, and recurrent selection. As noted above, such breeding methods are known to those of skill in the art. In conjunction with these steps, techniques such as RFLP-enhanced selection, genetic marker enhanced selection (for example, SSR markers), and the making of double haploids may be utilized.

In another aspect the method includes producing a population of progeny shallot plants of one or more of the shallot varieties disclosed herein, comprising crossing one or more of the shallot varieties disclosed herein with another shallot plant, thereby producing a population of shallot plants, which, on average, derive 50% of their alleles from the shallot varieties disclosed herein. A plant of this population may be selected and repeatedly selfed or sibbed with a shallot plant resulting from these successive filial generations, or may be backcrossed with a recurrent parent (one or more of the shallot varieties disclosed herein). One aspect of this invention is the shallot produced by this method and that has obtained at least 50%, at least 60%, at least 70%, at least 80%, at least 90% or more, all subranges and percentages therebetween inclusive, of its alleles from the shallot varieties disclosed herein. Methods for determining genetic makeup (genotyping) of a shallot plant are disclosed in, for example and without limitation, Reflinur et al., "Phenotypic Evaluation and Genetic Profiling of Shallot Genotypes Adapted to Peatland of South Kalimantan Using Simple Sequence Repeat (SSR) Markers," Agrivita, Journal of Agricultural Science 2019, 41(1), which is incorporated by reference herein in its entirety.

One of ordinary skill in the art of plant breeding would know how to evaluate the traits of two plant varieties to determine if there is no significant difference between the two traits expressed by those varieties. Thus, the present invention includes progeny of the shallot varieties disclosed herein comprising a combination of at least two traits of the shallot varieties disclosed herein selected from those listed in Table 1, so that said progeny shallot plant is not significantly different for said traits than the shallot varieties disclosed herein, as determined at the 5% significance level when grown in the same environmental conditions. Using techniques described herein, molecular markers may be used to identify said progeny plant as progeny of one or more of the shallot varieties disclosed herein. Mean trait values may be used to determine whether trait differences are significant, and preferably the traits are measured on plants grown under the same environmental conditions.

What is claimed is:

1. A seed of shallot variety 'Innovator,' wherein a representative sample of seed of said variety was deposited under NCIMB Accession No. 43895.

2. A shallot plant, part thereof, or tissue culture produced by growing the seed of claim 1.

3. A tissue culture produced from protoplasts or cells from the plant of claim 2, wherein said cells or protoplasts are produced from a plant part selected from the group consisting of leaf, pollen, embryo, cotyledon, hypocotyl, meristematic cell root, root tip, pistil, anther, ovule, flower, shoot, stem, seed, and petiole.

4. A shallot plant regenerated from the tissue culture of claim 3, wherein the plant has all of the morphological and physiological characteristics of variety 'Innovator'.

5. A method of producing a shallot seed comprising crossing two shallot plants and harvesting the resultant shallot seed, wherein at least one of the two shallot plants is the shallot plant of claim 2.

6. The method of claim 5, wherein one of the two shallot plants is a shallot plant that is unrelated to variety 'Innovator'.

7. The shallot seed produced by the method of claim 5.

8. A shallot plant, part thereof, or tissue culture produced by growing the seed of claim 7.

9. A method of introducing a desired trait into shallot variety 'Innovator,' comprising:
   (a) crossing a shallot plant of variety 'Innovator' wherein a representative sample of seed was deposited under NCIMB Accession No. 43895, with a plant of another shallot variety that comprises a desired trait to produce progeny plants, wherein the desired trait is selected from a group consisting of male sterility, herbicide resistance, pest resistance, and resistance to bacterial disease, fungal disease, or viral disease;
   (b) selecting one or more progeny plants that have the desired trait to produce selected progeny plants;
   (c) crossing the selected progeny plants with the shallot plant of variety 'Innovator' to produce backcross progeny plants;
   (d) selecting for backcross, progeny plants that have the desired trait and all of the physiological and morphological characteristics of shallot variety 'Innovator'; and
   (e) repeating steps (c) and (d) two or more times in succession to produce selected third or higher backcross progeny plants that comprise the desired trait and all of the physiological and morphological characteristics of shallot variety 'Innovator'.

10. A shallot plant produced by the method of claim 9, wherein said shallot plant has the desired trait.

11. The shallot plant of claim 10, wherein the desired trait is one or more of herbicide resistance, pest resistance, and male sterility.

12. A seed, plant part, or tissue culture of the plant of claim 10.

* * * * *